United States Patent [19]

Kametaka et al.

[11] Patent Number: 4,965,262

[45] Date of Patent: Oct. 23, 1990

[54] METHOD FOR TREATING OR PREVENTING LOCALLY PERIODONTAL DISEASE

[75] Inventors: Shigeru Kametaka, Kashiwara; Tadaaki Miyazaki, Osaka; Shinichi Hayashi, Fujiidera; Akira Handa, Funabashi; Kinya Kameda, Narashino, all of Japan

[73] Assignees: Rohto Pharmaceutical Co., Ltd., Osaka; Daiichi Pharmaceutical Co., Ltd., Tokyo, both of Japan

[21] Appl. No.: 159,905

[22] Filed: Feb. 24, 1988

[30] Foreign Application Priority Data

Feb. 26, 1987 [JP] Japan ................................ 62-43391

[51] Int. Cl.$^5$ ................................................ A61K 7/16
[52] U.S. Cl. ............................... 514/230.2; 514/900; 514/902
[58] Field of Search ................... 514/230.2, 900, 902; 424/52

[56] References Cited

U.S. PATENT DOCUMENTS

| | | | |
|---|---|---|---|
| 3,984,548 | 10/1976 | Gerster | 514/230.2 |
| 4,551,456 | 11/1985 | Katz | 514/912 |
| 4,701,320 | 10/1987 | Hasegawa et al. | 514/900 |
| 4,762,831 | 8/1988 | Grohe et al. | 514/230.2 |
| 4,772,470 | 9/1988 | Inoue et al. | 424/81 |

FOREIGN PATENT DOCUMENTS

| | | | |
|---|---|---|---|
| 58-62113 | 4/1983 | Japan | 514/230.2 |
| 58-072588 | 4/1983 | Japan | 514/230.2 |
| 58-210092 | 12/1983 | Japan | 514/230.2 |
| 61-148125 | 7/1986 | Japan | 514/900 |

OTHER PUBLICATIONS

Hirota et al., GA 109:156275y (1988) of JP 63,08,333 14 Jan. 1988 Topical Bactericides Containing Ofloxacin Gel.

Seibert et al., GA 109:79739y(1988) of Ger. Offen 3, 635, 453 11 Feb. 1988.

*Primary Examiner*—Shep K. Rose
*Attorney, Agent, or Firm*—Burns, Doane, Swecker & Mathis

[57] ABSTRACT

A method for treating or preventing periodontal disease which comprises administering ofloxacin or salts thereof locally to periodontal tissue are disclosed. The method is excellent on the treatment of periodontal disease in small dose without disturbance of bacterial flora.

2 Claims, No Drawings

METHOD FOR TREATING OR PREVENTING LOCALLY PERIODONTAL DISEASE

BACKGROUND OF THE INVENTION

1. Field of the Invention

The present invention relates to a method for treating or preventing locally periodontal disease. In particular, the present invention relates to a method for treating or preventing periodontal disease which comprises administering ofloxacin (9-fluoro-2,3-dihydro-3-methyl-10-(4-methyl-1-piperazinyl)-7-oxo-7H-pyrido[1,2,3-de][1,4-]benzoxazine-6-carboxylic acid) or salts thereof to periodontal tissue of a patient having periodontal disease.

2. Description of the Prior Art

Periodontal disease and dental caries are the two most common diseases in the dental field. In most cases, tooth loss in adults is caused by periodontal disease. Periodontal disease is an inflammatory disease on periodontal tissue such as the gingiva, and includes various types which vary depending on the progress degree of the disease or the age of the patient. Generally, those types can be mainly classified into gingivitis and periodontitis. Further, periodontitis can be classified into adult periodontitis and juvenile periodontitis.

Previously, it was hypotherized that periodontal disease was caused by non-specific stimulation derived from dental calculus or dental plaque. However, recent intensive bacteriological and immunochemical investigation have made it apparent that some specific bacteria among more than 200 kinds of bacteria, which exist in the dental plaque, relate to the occurrence of periodontal disease.

Particularly, as those bacteria, Actionmyces group, Spirochetes group, and gram negative bacteria such as Bacteroides group, Actinobacillus group, Fusobacterium group, Capnocytophaga group, Eikenella group are noted.

Further, relationships between some bacteria and some periodontal diseases have been reported. For example, *Bacteroides gingivalis* is supposed to relate to occurrence of adult periodontitis and *Actinobacillus actinomycetemcomitans* is supposed to relate to occurrence of juvenile periodontitis.

Periodontal disease has been treated by the following methods;

(1) Scaling for the purpose of removing sub-gingival plaque and dental calculus from periodontal pockets, (2) Gingivectomy for the purpose of removing the inflammatory tissue or periodontal pocket, and, (3) Root planning for the purpose of mechanically grinding the surface of the dental roots to accelerate the adhesion of the gingiva on the dental roots.

These methods are effective to some extent. However, some patients with specific internal diseases, for example a circulatory disease cannot undergo those surgical operations.

Further, as treating agents for periodontal disease, dentifrices containing a germicide or antiinflammatory agent, and pastes for massaging the gingiva have been used. However, these agents are not yet satisfactory for the treatment of periodontal disease. Under these circumstances, a method for treating periodontal disease, which is more effective than hose mechanical or surgical methods, is strongly desired.

As described above, specific bacteria relate to the occurrence of periodontal disease. Therefore, it is supposed to be effective for the treatment of periodontal disease to apply an antibacterial agent such as antibiotics in a suitable form to treat at an effective concentration the lesions of periodontal disease. However, this method has not been conducted for the following reasons:

(i) The bacteria which cause periodontal disease have not been identified.

(ii) Periodontal disease is usually classified into a chronic inflammatory disease and, it takes a long time to treat that disease. Therefore, when an antibacterial agent is given over a long period, a side effect of the agent may appear, or an opportunistic infection may appear by a disturbance of normal bacterial flora in the oral cavity and intestines.

(iii) No suitable administration method has been proposed. The bacteria which cause periodontal disease exists in the periodontal pockets between the teeth and the gingiva. Since the pockets are anatomically outer parts of the body, antibacterial agents are not delivered effectively to them when it is administered orally or by injection. Furthermore, even when they are administered in the form of a dentifrice, mouth wash or gingival massaging agent, they are not substantially delivered to the periodontal pockets and further, they are removed rapidly by the washing effect of saliva. Therefore, an effective concentration of antibacterial agents in the lesions of periodontal disease cannot be maintained.

After intensive investigations to solve these problems, the inventors have found that ofloxacin or salts thereof exhibit strong antibacterial effects against those bacteria and that when they are administered locally to lesions of periodontal disease, specifically to the periodontal pockets, remarkable effects on the treatment of periodontal disease are obtained.

SUMMARY OF THE INVENTION

This invention relates to a method for treating or preventing periodontal disease which comprises administering ofloxacin or salts thereof locally to periodontal tissue.

DESCRIPTION OF THE PREFERRED EMBODIMENTS

Examples of the salts of ofloxacin include acid addition salts thereof with an inorganic acid such as hydrochloric and sulfuric acid or an organic acid, and carboxylate with alkali metals or alkaline earth metals such as sodium, potassium and calcium.

Typical examples of the pharmaceutical preparations for administering ofloxacin or salts thereof locally to periodontal tissue include gels for the oral cavity, ointments adhesive to the membrane of the oral cavity, preparations to be inserted into periodontal pockets and tapes to be adhered to the gingiva.

The preparations for local administration can be prepared by mixing an active ingredient, that is, ofloxacin or salts thereof with excipients or vehicles used for preparations to the oral cavity by using conventional methods.

The preferred excipients and vehicles for those preparations include hydroxypropylcellulose, methylcellulose, hydroxymethylcellulose, sodium carboxymethylcellulose, hydroxypropylmethylcellulose, liquid paraffin, white petrolatum, plastibase, Eudragit L, sodium alginate, propylene glycol alginate, pullulan, tragantha, xanthane gum, chitosan, polyvinyl pyrrolidone, polyvinyl alcohol, polyacrylic acid, polymethacrylic acid, ethyl methacrylate, dimethylamino acetate, cellulose acetate, polyethyleneglycol, collagen and atelocollagen.

These substances can be used either respectively or as a combination of two or more kinds thereof. The combination is suitably selected depending on the preparation form. Those preparations may contain a coloring agent or a perfume as an additive. Typical examples of those preparations are shown below.

On the administration of those preparations, the gels or ointments are spread to the gingiva, the tapes are adhered to the gingiva and the preparations to be inserted into the pockets are inserted therein.

The dose varies depending on the degree of periodontal disease. Usually, a suitable amount of the preparation containing at least 0.01 wt % of ofloxacin is applied to the lesions of periodontal disease.

Ofloxacin has already been used clinically as an excellent synthetic antibacterial agent by oral administration. Acute toxicity ($LD_{50}$ in oral administration) of olfoxacin is 5,450 mg/kg in mice, 200 mg/kg or more in dogs and 500 to 1,000 mg/kg in monkeys.

According to the present invention, a method for treating or preventing periodontal disease, which exhibits very excellent effects without disturbance of bacterial flora even in a small dose, can be obtained.

Also, according to the present invention, the excellent effective concentrations of ofloxacin or salts thereof in periodontal tissue are kept compared to that obtained by administering those compound orally or in the form of injections.

The following examples will further illustrate the present invention, but by no means limit the invention.

EXAMPLES

Example 1

Gels for the oral cavity:

945 g of water was added to 50 g of high molecular weight hydroxypropylcellulose to prepare a gel. 5 g of ofloxacin was added to the gel to produce a homogeneous mixture to be used as the gels for the oral cavity.

Example 2

Ointments adhesive to the mucous membrane of the oral cavity:

313 g of liquid paraffin was added in small portions to 30 g of ofloxacin to obtain a mixture. 115 g of white petrolatum and 229 g of plastibase were added to the mixture and the obtained mixture was kneaded. Further, 313 g of sodium carboxymethylcellulose was added thereto and the mixture was thoroughly kneaded to obtain a homogeneous ointment.

Example 3

Preparations to be inserted into the periodontal pockets:

250 g of Eudragit L30D-55 (30% dispersion), 5 g of ofloxacin and 20 g of Tween 80 were mixed together. By using a casting method a film having a thickness of 300 μm was prepared from the mixture. The film was cut into strips having a width of 1 mm and a length of 10 mm to be inserted into the periodontal pockets.

Example 4

Tapes to be adhered to the gingiva:

85 g of a low molecular weight hydroxypropylcellulose was dissolved in 1,000 ml of water to form a gel. 5 g of ofloxacin and 10 g of polyethylene glycol 400 were mixed therein. The mixture was formed into a film having a thickness of 300 μm by the casting method. The film was cut into strips having a width of 10 mm and a length of 100 mm to be used as tapes to be adhered to the gingiva.

Test Example 1

Effects of gels containing ofloxacin on experimental periodontitis:

The effects of the gel preparation containing ofloxacin on experimental periodontitis of hamsters infected with *Actinomyces viscosus* (hereinafter referred to as *A. viscosus*) were examined.

18 male golden Syrian hamsters (3-week-old) were fed with an ordinary solid diet, CE-2 (CLEA Japan Co.) for two weeks, and were given penicillin G solution (4000 U/ml) freely for three days before the infection so as to control the indigenous bacterial flora and to facilitate the infection. The hamsters were then randomly assigned to one of the following three groups: an infected group to be treated, an infected group not to be treated and a non-infected group, each group comprising six hamsters. The oral cavity of each animal of the infected groups was inoculated with 0.25 ml of culture broth ($2.5 \times 10^8$ colonyl forming unit/ml; hereinafter CFU/ml) of *A. viscosus* ATCC 15987. The bacterial inoculation was performed daily for five days. From the first day of the infection, all animals were fed with Diet 2050 in place of feed CE-2. Diet 2050 was a powdery periodontitis-inducing feed comprising 28% of sucrose, 28% of corn starch, 28% of skim milk powder, 6% of flour, 4% of beer yeast, 3% of alfalfa powder, 1% of liver powder and 2% of common salt. After two weeks, 0.1 ml/day of the gels prepared in Example 1 was spread to the gingiva of each hamster everyday.

Eleven weeks after the first bacterial inoculation, the salivary occult blood degree of each animal was evaluated with occult blood test papers (Hemasticks III; Miles Sankyo Co.) under anesthesia, and the results were classified into five ranks of 0 to 4 according to the color standard. The gingival index was evaluated and assigned into 4 ranks of 0 to 3 macroscopically according to the criteria of Rosenberg et al. (J. Periodontol, 37: 208, 1966). Then, all the hamsters were decapitated. Dental plaque was scratched off throughly from the first molar of the left maxilla of each hamster, and was immediately suspended in an anaerobic Ringer's solution. A 10 fold dilution series was prepared in an anaerobic glove box. The total number of the bacteria was enumerated on a GAM agar culture medium (Nissui Seiyaku Co.), the number of *A. viscosus* was enumerated on a selective medium for *A. viscosus* (J. Clin. Microbiol., 15: 253, 1982) and the number of black-pigmented Bacteroides was enumerated on Kanamycin-Vancomycinmenadion-blood agar medium (BBL Co.). The plaque index was evaluated by the method of Regolati and Hotz (Helv. Odonto. Acta, 16: 13, 1972) after staining the teeth with a colorant (Red-Cote; Butler Co.). After evaluation of the plaque index, the jawbones were taken out. The soft tissue and debris were removed from the left jawbone to make a bone specimen. A macrograph of the each jaw was taken with a stereomicroscope along the lingual aspect. Measurements of the distances from the cement-enamel junction to alveolar crest were done for all lingual roots of molars on the macrograph. The sum of these distances in each hamster was calculated to determine the alveolar bone loss vale. On the other hand, the right jaw was fixed in formalin, dehydrated, decalcified and embedded in paraffin. It was then sectioned and stained with haematoxylin and eosin. Histological observation of the samples was conducted with a microscope.

As shown in Table 1, the degree of the periodontitis in the treated group was lower than that in the untreated, infected group with respect to the salivary occult blood which indicated hemorrhage from the gingival crevice, gingival index indicating the degree of inflammation of the gingiva, the plaque index indicating the quantity of the plaque, and the alveolar bone loss which is especially peculiar to periodontitis. The condition of the periodontal tissue in the treated group was similar to that of the non-infected group.

The counts of bacteria in the plaque in the respective groups are shown in Table 2. In the treated group, the counts of $A.$ $viscosus$ used for the infection and black-pigmented Bacteroides, whose pathogenicity in periodontitis has been noted, were quite small, though the total counts of bacteria was only slightly lower than that in the infected group.

In the histological observation, the deposition of a large amount of the plaque and emigration of polymorphonuclear leucocytes were observed in the infected group, proving presence of periodontitis, though these are not shown in the tables. On the contrary, they were only slight in the treated group and the degrees thereof were similar to those of the non-infected group.

These results indicate that the local administration of ofloxacin gel is effective on periodontal disease, particularly, periodontitis.

Test Example 2

Comparison of the concentrations of ofloxacin in the oral cavity by oral administration and local administration:

The preparations of Example 3 containing ofloxacin to be inserted into the periodontal pockets were locally administered to the pockets of volunteers and the concentration of ofloxacin in the periodontal fluid in the pockets was determined and compared with that in saliva obtained by oral administration thereof. In the test, the preparations of Example 3 having a thickness of 0.3 mm and width of 1 mm was cut into strips having a length of 4 mm (each containing 0.06 mg of ofloxacin). The strip was inserted into a periodontal pocket of each volunteer. The probing depth of the pocket was 5 mm.

After a given time, a filter paper having a width of 1 mm was inserted into the pocket to take the periodontal fluid out of the pocket. The amount of ofloxacin in the periodontal fluid was determined from the diameter of an inhibition circle according to an agar plate diffusion method with $E.$ $coli$ K 12. The quantity of the periodontal fluid thus taken out was determined from a calibration curve prepared from the quantity of a previously prepared liquid sample and the wetted area of the filter paper. The concentration of ofloxacin was thus determined. The time profile of the concentration of ofloxacin in saliva in the oral administration was taken from a report of Morihana et al. (Chemotherapy, 32: Sl, 1070, 1984).

The results are shown in Table 3. When 0.06 mg of ofloxacin was locally inserted into the periodontal pocket, the concentration thereof in the pocket was maintained above 70 $\mu$g/ml for longer than 5 h and 16.6 $\mu$g/ml even after 24 hours, while the maximum concentration in saliva was 1.8 $\mu$g/ml in 3 hours after the oral administration of 200 mg thereof. Namely, when ofloxacin in an amount of less than 1/3,000 of that given by the oral administration was inserted in the periodontal pocket according to the local administration, the concentration thereof in the pocket could be kept higher than that obtained by the oral administration. The concentration of ofloxacin in the periodontal pockets can be maintained for a longer period of time by varying the composition of the high molecular vehicles.

TABLE 1

| Group | Weight Gain[a] (g) | Salivary Occult Blood Degree[b] | Gingival index[b] | Plaque Index[a] | Alveolar Bone Loss Value[a] (mm) |
|---|---|---|---|---|---|
| Treated Group | 87.1 ±6.2 | 2.67 ±0.21 }** | 1.50 ±0.22 }* | 37.8 ±3.7 }*** | 7.59 ±0.50 } }* |
| Infected Group | 87.5 ±6.9 | 3.83 ±0.17 | 2.67 ±0.21 }* | 71.2 ±6.2 }* | 9.54 ±0.51 }* |
| Non-infected Group | 91.7 ±5.6 | 3.00 ±0.41 | 1.00 ±0.00 | 32.0 ±3.7 | 5.04 ±0.27 |

Each value is the mean ± standard error.
a: Examined by Student's t test. *; $p \leq 0.0001$, ; $0.001 \leq p \leq 0.01$, *; $0.01 \leq p \leq 0.05$
b: Examined by Mann-Whitney's U test. **; $0.001 \leq p \leq 0.01$, *; $0.01 \leq p \leq 0.05$

TABLE 2

Comparison of numbers of bacteria in dental plaques

| Group | Logarithmic number of bacteria (CFU/ml) | | |
|---|---|---|---|
| | Total Bacteria | A. Viscosus | Black-pigmented Bacteroides |
| Treated Group | 6.12± 0.43 | 4.76± 0.53 | <3.00 * |
| Infected Group | 6.86 ± 0.18 | 6.29 ± 0.31 | 5.53 ± 0.16 |
| Non-infected Group | 4.23 ± 0.81 | <3.00 * | <3.00 * |

* No colony was formed at all from the Ringer's solution diluted to $1/10^3$ or less. The other values are logarithmic number of bacteria in the Ringer's solution, and are expressed in the form of the mean ±standard error (CFU/ml).

TABLE 3

Influence of the administration method on change of concentration of ofloxacin in the oral cavity

| Administration method | Oral administration* | Local administration** |
|---|---|---|
| Dose | 200 mg/body | 0.06 mg/pocket |
| Subject (part) | 8 subjects (average body weight: 60.6 kg) | 8 periodontal pockets of 4 subjects (average depth of the pockets: 5 mm) |

TABLE 3-continued

Influence of the administration method on change of concentration of ofloxacin in the oral cavity

| Preparation given | | Ofloxacin powder | Preparations of Example 3 |
|---|---|---|---|
| Time after administration (h) | 1 | 1.18 | 72.1 |
| | 2 | 1.59 | 88.1 |
| | 3 | 1.80 | 84.0 |
| | 4 | 1.65 | 83.3 |
| | 5 | 1.40 | 76.5 |
| | 24 | ND | 16.6 |

*According to the report of Morihana et al. (Chemotherapy 32: S1, 1070 to 1083, 1984). The numerals are the average concentrations (μg/ml) of ofloxacin in saliva given by the oral administration method.
**The numerals are the average concentration (μg/ml) of ofloxacin in the periodontal fluid in the pockets after insertion of the preparations of Example 3 (1 mm width × 0.3 mm thickness × 4 mm length into the periodontal pockets.

What is claimed is:

1. A method for treating periodontal disease which comprises administering topically by insertion into a periodontal pocket an effective amount of ofloxacin or salt thereof to treat periodontal tissue to a patient in need of such treatment.

2. A method as claimed in claim 1, wherein ofloxacin or salt thereof is present in a range of 0.01 to 5 wt. %.

* * * * *